United States Patent [19]

Lidow

[11] 4,228,806
[45] Oct. 21, 1980

[54] SLEEP STATE INHIBITED WAKE-UP ALARM

[75] Inventor: Derek Lidow, Beverly Hills, Calif.

[73] Assignee: International Rectifier Corporation, Los Angeles, Calif.

[21] Appl. No.: 909,580

[22] Filed: May 25, 1978

[51] Int. Cl.³ .............................................. A61B 5/04
[52] U.S. Cl. ...................................... 128/731; 368/12; 368/244
[58] Field of Search ................. 128/2.1 B, 2.1 M, 1 C, 128/2.1 R, 731–733; 364/415–417; 340/279; 58/152 R, 152 B, 16 R

[56] References Cited

U.S. PATENT DOCUMENTS

| | | | |
|---|---|---|---|
| 3,584,618 | 6/1971 | Reinhard et al. | 128/DIG. 29 X |
| 3,618,592 | 11/1971 | Stewart et al. | 128/DIG. 29 X |
| 3,910,258 | 10/1975 | Pisarski et al. | 128/2.1 B |

OTHER PUBLICATIONS

Dikmen, F. N., "Getting a Better Sleep," *Industrial Research New Products Annual,* Sep. 1973, p. 47 & brochure therefore.
Courtney, P. et al., "A Hybrid Computer System for Unsupervised Scoring of Sleep Records," Proc. 9th Annual Rocky Mtn. Bioeng. Symp. & 10th Intnl. ISA Biomed. Sci. Instr. Symp., vol. 9, Omaha, Neb., 1–3 May, 1972, pp. 161–167.
Feedman, A. M. et al., "Modern Synopsis of Psychiatry," William & Wilkins Co., Balt. Md., 1972, pp. 30–35.

*Primary Examiner*—Robert W. Michell
*Assistant Examiner*—Francis J. Jaworski
*Attorney, Agent, or Firm*—Ostrolenk, Faber, Gerb & Soffen

[57] ABSTRACT

A wake-up alarm is set to ring in some time interval. One or more physical characteristics of the sleeping subject, including brain wave activity, pulse rate, REM activity, muscle tension, body temperature, hearing acuity, positional changes and the like are monitored to determine whether the subject is in a deep or shallow-sleep phase. If the subject is in the deep-sleep phase throughout the alarm time interval, the alarm is inhibited until the end of the alarm interval. The inhibiting of the alarm ends as soon as the subject goes into a shallow-sleep phase.

15 Claims, 4 Drawing Figures

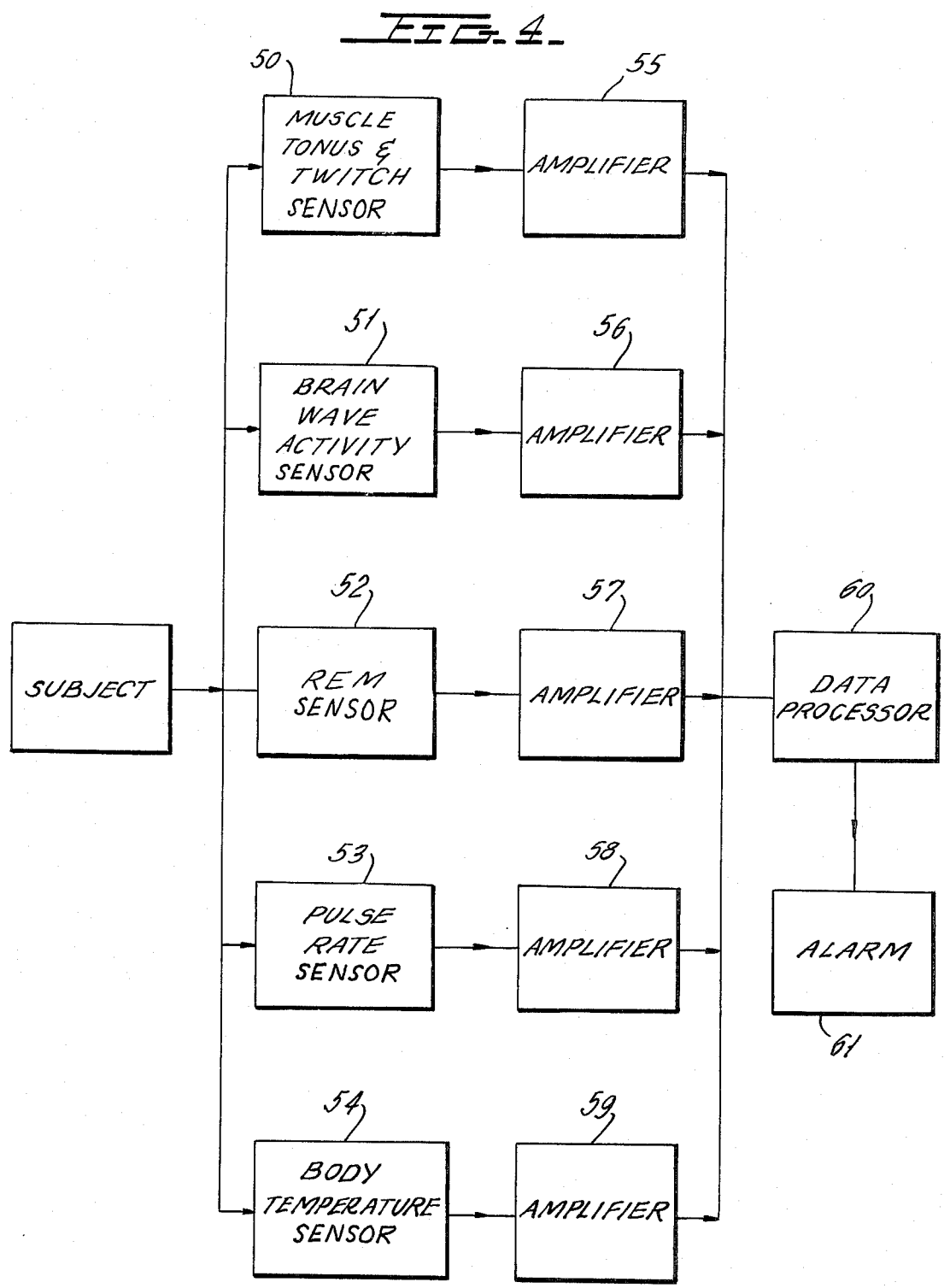

SLEEP STATE INHIBITED WAKE-UP ALARM

BACKGROUND OF THE INVENTION

This invention relates to a wake-up alarm, and more specifically relates to a wake-up alarm which is inhibited while the subject is in a deep-sleep phase.

When a human sleeps, he passes through different sleep phases which include a deep-sleep, rapid eye movement (REM) sleep and shallow-sleep phases. The phases can be identified by the state of one or more of several physical or physiological conditions including brain wave activity, REM, pulse rate, muscle tension, body temperature, hearing acuity, blood pressure, respiratory rate, body position changes, and others. As a specific example, when a human sleeps, he passes through a deep-sleep phase characterized by delta brain-wave frequencies which are less than about 4 hertz, and more shallow sleep phases characterized by the relatively high frequencies known as beta brain-wave frequencies, which are greater than about 13 hertz. REM sleep resembles a shallow-sleep phase when only brain waves are considered. However, the presence of REM or the absence of muscle tension or other indicators can be used to detect REM phase sleep.

The deep-sleep and REM phases are relatively short and it is believed that these are the most efficient sleep phases. It is desirable that a subject is awakened from sleep during the light-sleep phase. This recognition, however, has never been implemented in connection with the waking up of a sleeping subject.

Many prior patents have been obtained for systems wherein an alarm is given or some other signal is produced in response to the monitoring of the brain waves of a subject which would indicate that he is falling asleep or that he is experiencing a medical catastrophy. These systems have obvious use in connection with the waking of a dozing driver or the monitoring of a patient who might, for example, be in an intensive care situation. These systems will normally produce an output signal in response to brain-wave frequencies such as beta frequencies which appear in a subject who supposedly is in an alert state and passes into a state of light sleep. There is no attempt, however, in these prior art arrangements of inhibiting the production of an output alarm while the subject is in a deep-sleep or REM phase.

Typical of prior art references which monitor a normally alert subject for change in brain-wave frequencies indicating either a state of drowziness or a medical catastrophy are U.S. Pat. Nos. 3,811,116; 3,863,243; 3,866,204; 3,875,929; 3,877,466; 3,890,957; 3,896,790; 3,924,606; 4,013,068; 4,037,586.

A typical circuit which can be used to indicate the presence of alpha activity is disclosed in the journal "Psychophysiology", Volume 8, Number 1 (1971), pages 107 to 112, entitled "A Hybrid Circuit to Indicate the Presence of Alpha Activity".

Another reference showing circuitry well suited for such applications is NTIS document number AD/A-002 665 "Spindle and Rapid Eye Movement Detectors for Use with Sleep Analyzers", by Joseph C. Christian. This document also references many other documents that give details about alternative circuits that may be used to decode sleep stage information from brain waves. Another method that can be used is described by Anand Kumar, "A Real-Time System for Pattern Recognition of Sleep Stages by Fuzzy System Analysis", contained in Pattern Recognition, Vol. 9 (1977), pages 43 to 46.

BRIEF DESCRIPTION OF THE PRESENT INVENTION

The present invention provides a novel wake-up alarm in which the subject is provided with a monitor for monitoring a physiological or physical condition of the human being which would indicate that he in in either a deep-sleep, REM sleep or shallow-sleep phase.

In one embodiment of the invention, the brain-wave activity of the sleeping subject is monitored and the output of a sensor pickup is connected, by light, inobtrusive conductors, or by a small radio transmitter to a bedside alarm. The presence of a shallow-sleep phase characterized by brain-wave frequency greater than about 13 hertz will then permit alarm operation in a preset alarm interval and/or the presence of a deep-sleep brain wave frequency of less than 4 hertz will inhibit the alarm during the alarm interval. Sleep states can be reliably indicated by considering only brain wave amplitude data. Such a system has been developed and demonstrated by A. Kumar, referred to above.

Other physiological and physical conditions can be monitored and used independently or in combination with one another to insure that the alarm will be inhibited during a deep-sleep phase, or alternatively that the alarm can be actuated during a shallow-sleep phase. Thus, muscle tonus can be measured as by a sensor ring on the subject's finger. The muscle tension will be decreased during the deep-sleep phase and a signal to this effect (or a signal of increased muscle tension in the shallow-sleep phase) can be used alone or in combination with other outputs to control the alarm. The sensor ring used to measure muscle tonus can also measure muscular twitch which will have an amplitude related to deep or shallow-sleep phases. The twitch-rate information can be processed along with other output information to determine whether or not the subject is in a shallow-sleep phase.

Another sleep phase which can be monitored in rapid eye movement (REM) sleep. An electroculagraph (EOG) sensing the presence of rapid eye movement can be used alone or in combination with other outputs to inhibit the alarm during an alarm interval. Note that sensors are known for monitoring REM which do not interfere with the subject's sleep.

Pulse rate is a further function which can be measured and which is related to the sleep phase of an individual. Pulse rate can be measured by pickup from a separate sensor fixed to the subject or from one of the other sensors, such as a muscle tonus sensor. Alternatively, the pulse rate sensor can be a sensitive sensor fixed to the subject's bed, and thus does not interfere at all with the subject's comfort. The pulse rate will increase when the subject enters a shallow-sleep phase, and can be monitored over a given interval, say 30 seconds, and the rate in succeeding intervals can be compared to seek a given change. The pulse rate information can be used alone, or with other information to make the sleep or shallow sleep determination for a particular subject.

Another parameter which can be measured is body temperature. Thus, it is known that body temperature drops to a minimum just before a subject is ready to waken. This can be used alone or in combination with the other parameters to control the waking of the subject.

A large number of other parameters can be monitored including hearing acuity, blood pressure, position change rate, respiratory rate and the like.

It should be noted that different combinations of parameters can be used for different subjects and that the output of one or more of the parameters can be adjusted to best satisfy the particular characteristics of the subject.

A conventional alarm which could be the usual alarm clock is then provided with means for setting an alarm time interval. That is to say, the alarm system is set to ring in a time ranging beginning, for example, at 7:00 a.m. and extending for the following 15 minutes, so long as the subject is not in a deep-sleep stage. Once the given time range has expired, however, the inhibiting of the alarm is defeated and the alarm is given regardless of the sleep stage of the subject. It is likely that the subject will be out of the deep-sleep phase at some time within the wake-up range so that the subject will not have a deep-sleep phase interferred with and he will wake up during a more shallow sleep phase and thus can be awakened more easily, and will feel more refreshed than if he had been awakened from sleep during the deep-sleep phase.

It should be noted that absolute accuracy or efficiency is not needed in carrying out the invention, and the invention will provide benefits to the subject over a long period of time so long as it generally limits the number of times the subject is awakened from a deep-sleep phase.

BRIEF DESCRIPTION OF THE DRAWINGS

FIG. 4 is a block diagram of a system of the invention using a plurality of monitored functions in combination with one another.

DETAILED DESCRIPTION OF THE DRAWINGS

Figure 1:
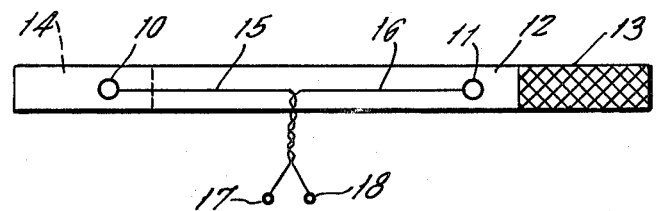
FIG. 1 illustrates an outstretched head band carrying spaced electrodes which can be used in accordance with the present invention for the pickup of brain waves of a sleeping subject.
Figure 2:
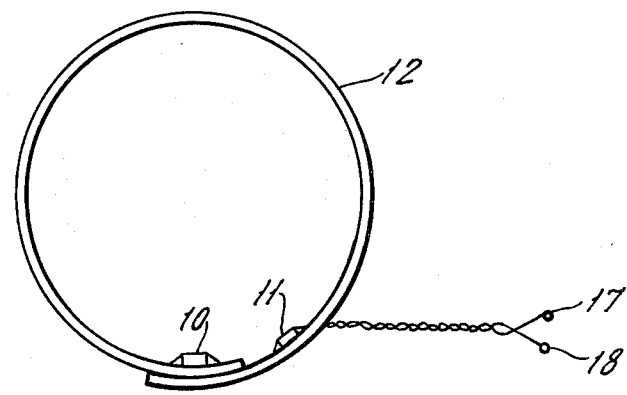
FIG. 2 shows the head band of FIG. 1 from the top after the head band has been joined at its opposite ends to form a closed ring.

Referring first to FIGS. 1 and 2, there is shown therein a typical sensor which can be used as a pickup for the brain waves of a sleeping subject. The sensor consists of two spaced electrodes 10 and 11 which are adapted to make good electrical contact with the skin in the supraorbital region of the head of a person. These electrodes can be small disks of sponge rubber wetted with saline solution or small metal disks attached to the surface of the skin with an adhesive tape. A good low-resistance contact can be provided by washing the skin with ether and applying a small amount of electrode jelly between the skin and the metal electrode in order to obtain a suitable low-resistance contact.

The electrodes 10 and 11 are fixed in a flexible fabric band 12 which may have hook and loop-type fasteners 13 and 14 at its opposite ends to enable the band to be snugly but comfortably fixed about the head of the subject, as shown in FIG. 2 and to insure that electrodes 10 and 11 stay in engagement with the subject's skin. Suitable electrode leads 15 and 16 extending from sensors 10 and 11 may be sewn into the head band 12 and extend outwardly for any desired length to the terminals 17 and 18, respectively, which can be connected to the monitoring apparatus at the subject's bedside. Note that other arrangements can be provided as desired for affixing electrodes to the subject to be monitored. Moreover, other systems for monitoring can be provided in addition to, or in place of, the brain-wave monitoring structure of FIGS. 1 and 2 as will be described.

It should be further noted that the output of the monitoring sensors can be connected to monitoring circuits by wires, such as the wires 15 and 16, or can, if desired, be coupled to a radio transmitter of extremely small size and low power which will transmit the necessary signals to a suitable receiving apparatus at the patient's bedside. This would then allow the patient more freedom for movement during sleeping and would make the attachment of the head band 12 more comfortable. Note that the head band 12 can be incorporated into a sleeping cap if desired.

Figure 3:
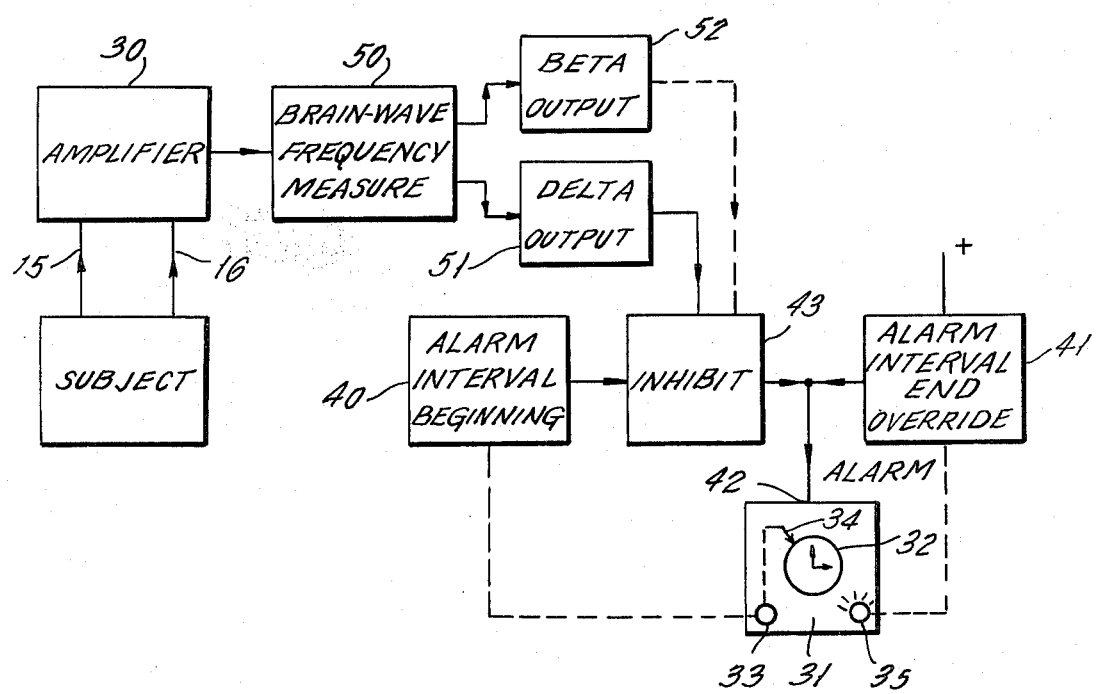
FIG. 3 is a block diagram of an electrical circuit which can be used to set an alarm and to inhibit the alarm during the deep-sleep phase of a sleeping subject in accordance with the present invention.

FIG. 3 shows a block diagram of a monitoring circuit which is constructed in accordance with the present invention. The essential purpose of this circuit is to distinguish between output signals which are greater than about 13 hertz (beta brain waves) or less than about 4 hertz (delta brain waves), and to produce a suitable output control signal in response to the presence or absence of one of these signals.

The output conductors 15 and 16 extending from the subject may be connected to a suitable amplifier 30 in FIG. 3. As previously pointed out, conductors 15 and 16 can be replaced by radio-transmitted signal systems.

The wake-up alarm is shown in FIG. 3 as a conventional alarm clock 31 having a clock display 32 which can have an alarm time set by the adjustment of an adjustment knob 33. Adjustment knob 33 rotates alarm indicator 34 relative to the time display 32 to set a future time at which the alarm 31 can ring.

Alarm 30 is also provided with an alarm interval setting mechanism 35 which is rotatable to adjust the alarm interval for some desired period within which the alarm can ring, where the interval may be as long, for example, as one-half hour. Thus, by rotating member 35 one can set the alarm interval within which the alarm can ring to between 0 minutes to 30 minutes following the beginning of the interval.

The alarm setting mechanism 33 is then connected to a signal-generating, alarm-interval-beginning circuit 40 which produces an output signal when the clock 32 indicates that the beginning of the alarm-interval time set by the member 34 has been reached, and the time at which the subject is to be awakened has arrived.

An alarm-interval-end-override circuit 41 is coupled to the mechanism 35 and is operable to apply an alarm signal to the alarm mechanism 31 at the end of the interval set by the mechanism 35 if the alarm has not been actuated by the signal coming from alarm-interval-beginning circuit 40.

The alarm is actuated by the mechanism 31 when a signal is applied to the alarm input 42. This signal may come through the inhibit circuit 43 which is connected to the alarm-interval-beginning circuit 40 or from the alarm-interval-end-override 41 once the alarm period has expired.

The output of amplifier 30 is connected to a suitable brain-wave frequency measuring circuit 50 which may take any desired form as shown in any of the previously mentioned references. The brain-wave frequency measuring circuit then produces an output signal through the circuit 51 if the output frequency of the amplifier 30 and thus that produced by the subject is lower than about 4 hertz, thus indicating that the subject is in the delta or deep-sleep phase. If this is the case, the circuit 51 energizes the inhibit circuit 43 to inhibit any signal from the alarm-interval-beginning circuit 40 from producing an alarm signal to the alarm input 42. Once, however, the subject is out of the deep-sleep phase, the signal output from the delta output circuit 51 disappears and the inhibit circuit 43 no longer inhibits the energization of the alarm 31 by the alarm-interval-beginning circuit 40.

Note that the brain-wave frequency measuring circuit 50 can also produce an output indicative of the subject being in the beta sleep phase which would correspond to a brain-wave frequency greater than about 13 hertz. The beta output circuit 52 can alternatively serve to actuate the circuit 43 which would then be arranged to be inhibited only in the absence of an output signal from circuit 52.

As a result of the circuit of FIG. 3, which can be constructed using any desired presently available circuit and alarm clock systems of well known types, the subject will be awakened during the time range which he previously set in the alarm 31, only when he is not in a deep-sleep or REM phase during that time range. If, however, he is not out of the deep-sleep or REM phase during the period, the alarm inhibit will be overridden by circuit 41 at the end of the range and the alarm will be given.

As pointed out previously, other physiological and physical qualities indicative of the sleep phases can also be used individually, or in any combination. Thus, as shown in FIG. 4, the subject can be connected to one or more of sensors 50 to 54 which correspond to muscle tone, brain wave, REM, pulse rate and body temperature functions respectively. The output of each of transducers 50 to 54 is connected to respective amplifiers 55 to 59 which can adjustably amplify or cut off its respective sensor to enable "tuning" of the sensors to the functions of a particular individual.

The output of each of the amplifiers 55 to 59 is then connected to data processor 60 which suitably processes the output of each of the sensor amplifiers 55 to 59. Thus, processor 60 will include circuitry to discriminate between beta and delta outputs from amplifier 56 and further can examine their waveforms to insure the existence of a shallow-sleep phase.

Data processor 60 will also analyze the output of REM amplifier 57 to determine a rapid eye movement phase by determining a reduction in REM activity preceding the deep-sleep phase and increased REM activity during the deep-sleep phase. This activity can be used with the data of any of the other sensors 50, 51, 53 and 54 to verify a REM phase to inhibit alarm system 61. Alarm system 61 may be similar to that of FIG. 3.

Data processor 60 will also process the pulse rate output from amplifier 58 and determine whether the rate is changing (by comparing the count made in each 30-second interval), and use that information alone or in combination with other outputs, to operate alarm 61.

In the same way, data from sensors 50 and 54 will be suitably processed by data processor 60 to control alarm 61.

Although a preferred embodiment of this invention has been described, many variations and modifications will now be apparent to those skilled in the art, and it is preferred therefore that the instant invention be limited not by the specific disclosure herein but only by the appended claims.

I claim:

1. A wake-up alarm comprising, in combination: sensor means associated with a subject and monitoring at least one characteristic of said subject related to the depth of sleep of said subject and delivering an output related to the depth of sleep of said subject; wake-up alarm means; adjustment means connected to said wake-up alarm means to enable said alarm means to sound an alarm at any time within a given time range; inhibit means connected to said wake-up alarm means for inhibiting the operation of said alarm within said given time range when said inhibit means is in a given energization state; signal-processing means connected to said sensor means and producing a first output signal when said sensor's output indicates that said subject is in a deep-sleep or REM state, and producing a second output signal when said sensor output indicates that said subject is in a sleep state shallower than said deep-sleep state; said output signals of said signal-processing means being connected to said inhibit means and causing said inhibit means to inhibit said alarm means when said subject is in said deep-sleep or REM state.

2. The device of claim 1 which further includes inhibit defeater means for defeating said inhibit means at the end of said given time range, whereby said alarm means produces a wake-up alarm, even though said subject is in a deep-sleep state at the end of said time range.

3. The device of claim 1 wherein said sensor means monitors brain-wave activity, and wherein said sensor means produces said first output signal when said subject is in a delta sleep phase.

4. The device of claim 3 which further includes inhibit defeater means for defecting said inhibit means at the end of said given time range, whereby said alarm means produces a wake-up alarm even though said subject is in a deep-sleep state at the end of said time range.

5. The device of claim 1 wherein said sensor means monitors brain-wave activity, and wherein said sensor means produces said second output signal when said subject is in a beta sleep phase.

6. The device of claim 5 which further includes inhibit defeater means for defeating said inhibit means at the end of said given time range, whereby said alarm means produces a wake-up alarm even though said subject is in a deep-sleep state at the end of said time range.

7. The device of claim 1 wherein said sensor means includes devices for monitoring at least two different sleep-related characteristics of said subject.

8. The device of claim 1 wherein said sensor means monitors pulse rate.

9. The device of claim 1 wherein said sensor means monitors REM.

10. The device of claim 1 wherein said sensor means monitors body temperature.

11. The device of claim 1 wherein said sensor means monitors muscle tonus.

12. The method of waking up a human subject from a sleeping phase; said method comprising the steps of setting a wake-up alarm to start after some given time; measuring at least one sleep-related characteristic of said human subject during at least said given time wherein said characteristic indicates whether said subject is in a deep-sleep, REM or shallow sleep phase; and inhibiting said alarm from starting while said subject is in a deep-sleep phase.

13. The method of claim 12 which includes the further step of causing said alarm to start after a given time period regardless of the state of said sleep-related characteristic of said subject.

14. The method of claim 12 wherein said characteristic is brain wave activity.

15. The method of claim 12 wherein at least two sleep-related characteristics are measured and wherein both of said at least two sleep-related characteristics must indicate that said subject is in said deep-sleep phase to inhibit said alarm.

* * * * *